US007508520B1

(12) United States Patent
Lines et al.

(10) Patent No.: US 7,508,520 B1
(45) Date of Patent: Mar. 24, 2009

(54) SYSTEM AND METHOD FOR MULTI-TARGET FLUID CONCENTRATION DETECTION AND MAPPING

(75) Inventors: Raymond Todd Lines, Rochester, NY (US); Norman A. Lopez, Rochester, NY (US); Joseph L. Lippert, Rochester, NY (US); Darryl Guy Murdock, Penfield, NY (US); Dawn Lenz, Erie, CO (US); Michael Stoogenke, Tully, NY (US); Matthew C. Severski, Fairport, NY (US); Hooshmand M. Kalayeh, Pittsford, NY (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 328 days.

(21) Appl. No.: 11/521,265

(22) Filed: Sep. 14, 2006
(Under 37 CFR 1.47)

(51) Int. Cl.
*G01N 21/00* (2006.01)
(52) U.S. Cl. .................... 356/437; 250/338.5
(58) Field of Classification Search ......... 356/432–444; 250/338.5, 372, 339.06, 339.11
See application file for complete search history.

(56) References Cited

U.S. PATENT DOCUMENTS

| | | | | |
|---|---|---|---|---|
| 4,772,789 | A * | 9/1988 | Maram et al. | 250/330 |
| 4,853,543 | A * | 8/1989 | Ozdemir | 250/372 |
| 6,822,742 | B1 | 11/2004 | Kalayeh et al. | |
| 6,995,846 | B2 * | 2/2006 | Kalayeh et al. | 356/437 |
| 7,260,507 | B2 * | 8/2007 | Kalayeh | 702/191 |
| 7,333,184 | B2 * | 2/2008 | Kalayeh | 356/4.07 |
| 7,375,814 | B2 * | 5/2008 | Reichardt et al. | 356/437 |
| 2006/0268947 | A1 * | 11/2006 | Kalayeh | 372/20 |
| 2007/0215795 | A1 * | 9/2007 | Kameyama et al. | 250/222.2 |

OTHER PUBLICATIONS

Daniel Brake et al., "New Airborne Remote Sensing Enhances Pipeline Integrity Assessment", Pipeline & Gas Journal, vol. 231 No. 6, Jun. 2004.

William B. Grant, "Effect of differential spectral reflectance on DIAL measurements using topographic targets", Applied Optics, vol. 21, No. 13, Jul. 1, 1982, pp. 2390-2394.

P. Vujkovic Cvijin et al., "Reflectance spectra of terrestrial surface materials at $CO_2$ laser wavelengths: effects on DIAL and geological remote sensing", Applied Optics, vol. 26, No. 19, Oct. 1, 1987, pp. 4323-4329.

(Continued)

*Primary Examiner*—Hoa Q Pham
(74) *Attorney, Agent, or Firm*—Ratner Prestia

(57) ABSTRACT

Methods and systems for obtaining a target fluid map of a survey area using a differential absorption LIDAR (DIAL) system are provided. Pulse bursts are transmitted toward the survey area, where each pulse burst includes an off-line pulse and at least one on-line pulse. Pulse bursts, each being associated with a measurement point, are received from the survey area. A concentration path length (CPL) corresponding to a respective on-line pulse, a spatial location associated with the CPL, and an error associated with the CPL are determined for each measurement point. The CPL for each measurement point is arranged within the survey area to form the target fluid map.

25 Claims, 12 Drawing Sheets

OTHER PUBLICATIONS

Syed Ismail et al., "Airborne and spaceborne lidar measurements of water vapor profiles: a sensitivity analysis", Applied Optics, vol. 28, No. 17, Sep. 1, 1989, pp. 3603-3615.

Norman A. Lopez et al., "Pulse Finding Apparatus and Method", U.S. Appl. No. 11/156,150, filed Jun. 17, 2005 (Not Published).

Hooshmand M. Kalayeh, "A Method for Improving the Performance Accuracy in Differential Absorption LIDAR for Oil and Gas Pipeline Leak Detection and Quantification", U.S. Appl. No. 11/223,241, filed Sep. 9, 2005 (Not Published).

* cited by examiner

SYSTEM AND METHOD FOR MULTI-TARGET FLUID CONCENTRATION DETECTION AND MAPPING

FIELD OF THE INVENTION

The present invention relates to remotely detecting fluid leaks in general and, specifically, to systems and methods for measuring and mapping fluid concentrations.

BACKGROUND OF THE INVENTION

Detection of fluid leaks, such as natural gas leaks from pipelines, is well known in the art. It is difficult to detect failures of gas and oil pipelines, because the gas or oil pipeline is typically buried beneath ground level. When failures do occur, they are manifest by the leakage of the pipeline contents, where the leaking material produces a characteristic trace or signal which may be measured. Because fluids can escape from a pipeline and travel through subterranean earth to the earth's surface and then into the atmosphere, the atmosphere can be monitored for the trace fluids.

Differential absorption LIDAR (DIAL) systems may be used to remotely measure the chemical composition of fluids in the atmosphere. DIAL systems may be provided on an airborne or a ground-based platform. In a DIAL system, at least two lasers having different wavelengths are transmitted to a survey area for trace fluid detection from a remote location. Although a DIAL system may use two or more lasers, it is understood that, in general, a DIAL system uses at least two different wavelengths for trace fluid detection. It is contemplated that a single laser may be used in a scheme similar to frequency hopping to select different wavelengths or may be tuned to different wavelengths. The wavelength of one of the lasers, referred to as the on-line laser, is typically selected to coincide with a strong absorption feature of the fluid to be detected. The wavelength of another of the lasers, referred to as the off-line laser, is typically selected such that it is not absorbed by the target fluid. The transmitted laser beams may be reflected, scattered and/or absorbed before being received by the DIAL system. If the target fluid is present, a portion of the transmitted on-line laser energy may be absorbed by the target fluid and the received energy may be different from the received off-line laser energy. If the target fluid is not present, both received laser energies may be approximately equal. A difference in received energies may be used to estimate a concentration path length (CPL) of the target fluid used for estimating a concentration of the target fluid.

Natural gas, for example, characteristically contains a mixture of methane, ethane, and small amounts of other gases. Oil pipelines also contain significant concentrations of volatile dissolved gas compounds, including methane, ethane, and propane. Gas may also be generated by the decomposition of organic matter, henceforth, referred to as swamp gas, and may only contain methane. Measurement of the expected components and a confirmation of the appropriate concentration ratio between these components can thus be used to directly establish the presence of a pipeline leak. It is contemplated that swamp gas may also be distinguished from a target fluid by observing a shape, spatially, of the emitted plume. Swamp gas may have a different shape as compared with a target fluid. In general, it is highly desirable for any fluid detection method to be able to distinguish between released gases resulting from a failure in a pipeline or a holding container versus emanating swamp gases, thus avoiding false alarms.

It will be appreciated that in many DIAL systems, the on-line returns are typically not much higher in energy than the background noise. This low signal-to-noise ratio (SNR), when the target fluid is present in the survey area, results in ambiguities or difficulties in detecting the on-line returns. Variation in spectral surface reflectivity typically causes a corresponding variation in the on-line and off-line returns. This variation is made more pronounced in the detection algorithm if the variation in the off-line is in an opposite direction as the on-line (e.g. the off-line reflectivity is higher and the on line reflectivity is lower). It is also made more pronounced if there is misalignment of the on-line and off-line beams (partially overlapping beams).

Low surface cover reflectivity results in low off-line and on-line returns whereas high surface cover reflectivity results in high returns. When the returned signal is low relative to noise, electrical noise may dominate and cause a low SNR and large CPL variance, but the opposite is also true. When the returns are high relative to noise, the signal dominates, leading to a high SNR and low CPL variance. Because the surface cover reflectivity varies from point to point and from region to region, so do the off-line and on-line returns and thus the SNR.

In practice, DIAL systems are calibrated. However, it may be difficult to correct for reflectivity variations due to the type of surface cover in many situations. If the surface cover reflectivity variations are not properly corrected, significant errors in CPL estimates of the target fluid may result, leading to false identification of target fluid plumes (or lack of plumes).

U.S. Pat. No. 6,822,742, issued on Nov. 23, 2004 to Kalayeh et al., entitled SYSTEM AND METHOD FOR REMOTE QUANTITATIVE DETECTION OF FLUID LEAKS FROM A NATURAL GAS OR OIL PIPELINE, provides a system for remote quantitative detection of fluid leaks from a natural gas or oil pipeline by use of an airborne platform. The contents of the above referenced application are incorporated herein by reference in their entirety.

SUMMARY OF THE INVENTION

The present invention is embodied in a method for obtaining a target fluid map of a survey area using a differential absorption LIDAR (DIAL) system. The method transmits a plurality of pulse bursts toward the survey area. Each transmitted pulse burst includes an off-line pulse and at least one on-line pulse. The method further receives a plurality of pulse bursts from the survey area. Each received pulse bursts is associated with a measurement point. The method determines, for each measurement point, a concentration path length (CPL) corresponding to a respective on-line pulse, a spatial location associated with the CPL, and an error associated with the CPL. The method arranges the CPL for each of the measurement points within the survey area to form the target fluid map.

The present invention is also embodied in a system for obtaining a target fluid map of a survey area using a DIAL system that transmits a plurality of pulse bursts toward the survey area. Each transmitted pulse burst includes an off-line pulse and at least one on-line pulse. The system includes an input terminal for receiving a plurality of pulse bursts from the survey area, where each pulse burst is associated with a measurement point. The system also includes a CPL estimator configured to determine, for each measurement point, a CPL corresponding to a respective on-line pulse and determine a spatial location associated with the respective CPL. The system further includes a quality factor error estimator configured to determine an error associated with the CPL for each of the measurement points and a CPL map generator configured to arrange the CPL, for each measurement point, within the survey area to form the target fluid map.

The present invention is further embodied in a CPL estimator for estimating at least one CPL from a pulse burst received from a DIAL system. The pulse burst includes an off-line pulse and at least one on-line pulse corresponding to a measurement point of a survey area. The CPL estimator includes a pulse finder configured to detect the off-line pulse and the at least one on-line pulse of the pulse burst. The CPL estimator further includes a pulse energy system configured to determine an off-line pulse energy and at least one on-line pulse energy associated with the detected off-line pulse and the detected at least one on-line pulse. The CPL estimator further includes a reflectivity ratio corrector configured to correct a reflectivity ratio parameter for the received pulse burst and a CPL processor configured to determine the at least one CPL using a ratio of the at least one on-line energy to the off-line energy, and the corrected reflectivity ratio parameter.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Figure 1:
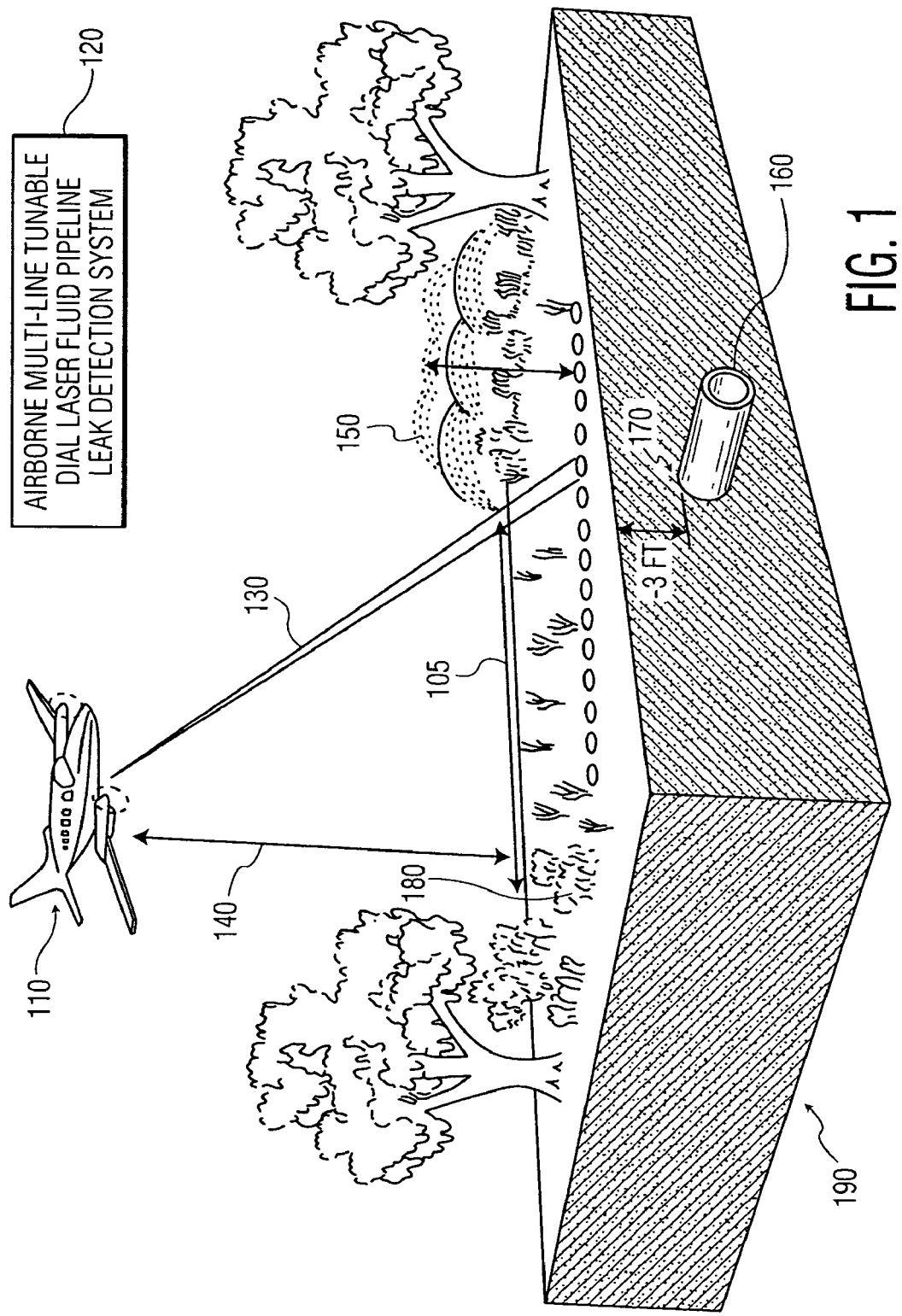
FIG. 1 is a schematic diagram illustrating an exemplary multi-line tunable DIAL laser fluid pipeline leak detection system aboard an airborne platform, according to an embodiment of the present invention.

The present invention described herein addresses the concentration detection of measured target fluids, for example trace gases associated with oil and gas leakages from pipelines. This invention relates to an oil and gas pipeline leak detection system and method of detecting gas concentration in the atmosphere and more particularly, but not by way of limitation, to mapping pipeline leak concentration over a survey area based upon differential absorption lidar (DIAL) sensing techniques operating in a mid-infrared spectral range.

In general, many fluids may be detected or explored, such as gas, volatile oil, light crude oil, heavy crude oil, hazardous gases, hazardous liquids, or chemical and biological agents. Gas concentrations, for example, may be mapped over an area and the maps may be analyzed for concentration anomalies. These gas anomalies may be interpreted to determine underground pipeline leaks.

As used herein, the term "target fluids" indicates fluids that are either liquids or gases, for example, target fluids associated either directly or indirectly with pipeline leaks. The measured atmospheric concentrations of these target fluids form the basis of the present invention. Each target fluid has some unique characteristics in its association with the pipeline leak. For example, methane is produced in a number of ways. Methane may occur in the atmosphere as a result of emission from a hydrocarbon deposit, emission from a coal deposit, emission from wetlands with active populations of methane producing bacteria, emission from a leaking natural gas pipeline, etc.

Sources of methane other than a pipeline leak are considered to be environmental interferences. Environmental interferences, which complicate the association between a target fluid and the pipeline leak, vary in magnitude and type according to factors such as soil type, hydrology, subsurface structure and composition, as well as atmospheric conditions, weather and land use.

The present invention may be configured as a differential absorption lidar (DIAL) system that samples a path through the atmosphere. According to an aspect of the present invention, a single pulse burst is transmitted for each measurement location within a survey area. Associated with each transmitted pulse burst, a multi-line laser radar may produce N on-line single pulses and at least one off-line pulse, where each on-line pulse is associated with a specific target fluid wavelength and the off-line pulse is associated with a wavelength that does not correspond to a target fluid. The present invention processes pulse burst returns from the multi-line laser radar to determine the presence of natural gas and other fluid leaks. The present invention estimates the concentration path length (CPL) for the N target gases and/or fluids. Each of the estimated CPL's may be assigned a geolocation and formed into a CPL spatial map over the survey area. The method may employ spatial image processing algorithms and noise reduction algorithms to reduce a noise level of the CPL spatial map and produce a two- or three-dimensional target fluid map. The target fluid map may also be combined with ancillary data.

FIG. 1 is a functional block diagram illustrating an exemplary multi-line tunable DIAL laser fluid pipeline leak detection system. Aircraft 110 includes an onboard multi-line tunable DIAL laser fluid pipeline leak detection system 120 which transmits laser beams 130 to detect trace gases 150 leaking from buried pipeline 160 in area 170 along ground surface 180. Also shown is a 3-dimensional section of the ground, generally designated as 190, including pipeline 160, leak area 170 and trace gases 150.

Based on a predetermined flight path, aircraft 110 flies at altitude 140 along ground track 105. During the flight, an onboard global positioning system (GPS) and inertial measurement unit (IMU) (not shown) guide the pilot along a target location following pipeline 160. When the aircraft reaches the target location, laser beams 130 are automatically pointed to the target, as the scanner system scans the surrounding target region. According to an embodiment of the present invention, a single pulse burst, further described below, is transmitted for each measurement location. The returned pulse is analyzed to develop target fluid concentration maps or images of the trace gas plumes in units of concentration path-length. In the example of FIG. 1, the returned pulse is analyzed to develop two- or three-dimensional gas-maps, i.e. fluid maps, or images of both methane and ethane plumes in units of concentration path-length.

Although FIG. 1 illustrates multi-line leak detection system 120 as being included in aircraft 110, it is contemplated that aircraft 110 may include any airborne vehicle, for example, a helicopter, or any spaceborne vehicle, for example, a satellite. A ground vehicle may also be included.

In a multi-tunable laser DIAL measurement system, in accordance with the present invention, multiple single-wavelength laser pulses are transmitted in one pulse burst. A laser pulse of a specific wavelength, i.e. $\lambda_1$, is chosen which is absorbed by one of the target fluids of interest to represent one of the on-line wavelengths. In general, the remaining laser pulses of the pulse burst are provided at different wavelengths, i.e. $\lambda_2 \ldots \lambda_N$, that are not absorbed by the specific target fluid corresponding to $\lambda_1$. It is contemplated that for more complex target fluids (i.e. target fluids having a broad spectral line), more than one wavelength may be selected to detect the target fluid. In an exemplary embodiment, a single on-line wavelength is selected for methane and three on-line wavelengths are selected for propane. An off-line wavelength, i.e. $\lambda_0$, is also provided which represents a non-target fluid wavelength. The energy reflected back to the sensor for each wavelength, i.e. $\lambda_0, \lambda_1, \ldots \lambda_N$, is measured and combined to generate an estimate of the target fluid concentration path lengths (CPLs).

CPL estimation for a single target fluid will now be discussed with respect to a 2-laser DIAL measurement system. It is understood that a similar process may be performed for a multi-laser DIAL measurement system to estimate respective CPLs for multiple target fluids, in accordance with the present invention.

In a 2-laser DIAL measurement system, two single-wavelength, laser pulses are transmitted. One laser pulse of a specific wavelength is chosen which is absorbed by the gas of interest. The other laser pulse is chosen at a different wavelength that is not absorbed by the target fluid of interest. The energies reflected back to the sensor for both wavelengths are measured and combined to generate an estimate of the target gas CPL.

Laser light transmitted from a LIDAR system may be reflected, absorbed, scattered and transmitted by the target. The light may be scattered back toward the LIDAR system through many mechanisms. Aerosol particles are a typical mechanism for scattering light toward the receiver. The scattering due to aerosol particles, however, typically produces a weak signal. A stronger signal may be produced by using a reflector surface. If two or more wavelengths of light are used, the difference in absorption of the light at the different wavelengths due to the target fluid may be used to determine how much target fluid is intersected by the transmitted light. The energy in a returned pulse burst may be given by:

$$E(\lambda, t) = \frac{E_L \rho(\lambda) D^2}{4 R_T^2} \xi(\lambda) \xi(R_T) \exp\left(-2 \int_0^{R_T} \kappa(\lambda, R) \, dR\right) \quad (1)$$

where $E_L$ is the laser output pulse energy, $\rho$ is the reflectivity of the surface at wavelength $\lambda$, $R_T$ is the range or distance to the surface, D is the aperture diameter (assuming a circular aperture). The terms $\xi(\lambda)$ and $\xi(R_T)$ represent the spectral response of the optical system and the receiver/laser geometric form factor. The exponential term represents the transmission of the laser light through the atmosphere.

A columnar measurement of the target fluid concentration, i.e. a CPL, may be defined as:

$$CPL = \int_0^R N(R) \, dR \quad (2)$$

where N(R) is the concentration of a fluid species in a volume, and R is the path of the laser light through the volume.

Differential absorption may be used to estimate the return energies for the on-line wavelength and the off-line wavelength. Let $E_1$ denote the return energy at the on-line wavelength and let $E_0$ represent the return energy at the off-line wavelength. Then, the ratio of $E_1/E_0$ is expressed by:

$$\frac{E_1}{E_0} = \quad (3)$$

$$\frac{\xi(\lambda_{on}) \xi_{on}(R_T) \rho_{on}}{\xi(\lambda_{off}) \xi_{off}(R_T) \rho_{off}} \times \exp\left(-2 \int_0^{R_T} (\kappa(\lambda_{on}, R) - \kappa(\lambda_{off}, R)) \, dR\right)$$

where $\kappa(\lambda_{on}, R)$ is the absorption coefficient for the on-line wavelength, $\kappa(\lambda_{off}, R)$ is the absorption coefficient of the off-line wavelength, $\rho_{on}$ is the reflectivity for the on-line wavelength and $\rho_{off}$ is the reflectivity for the off-line wavelength. Taking the log of both sides and rearranging terms yields $$\frac{1}{2} \ln\left(\frac{E_1}{E_0} C_\rho\right) = \int_0^{R_T} (\bar{\kappa}(\lambda_{on}, R) - \bar{\kappa}(\lambda_{off}, R)) \, dR + \quad (4)$$
$$\int_0^{R_T} N(R)(\sigma_a(\lambda_{on}) - \sigma_a(\lambda_{off})) \, dR$$

where

-continued $$C_\rho = \frac{\rho_{on}}{\rho_{off}} \quad (5)$$

and where $C_\rho$ is the reflectivity ratio, N(R) is the concentration of the desired target fluid and $\sigma(\lambda_{on})$ and $\sigma(\lambda_{off})$ are the molecular absorption cross sections of the on-line and off-line wavelengths, respectively. The quantities $\kappa(\lambda_{on},R)$ and $\kappa(\lambda_{off},R)$ are the absorption coefficient of all atmospheric gases other than the target. Equation (4) assumes that $\xi(\lambda_{on}) = \xi(\lambda_{off})$ and $\xi_{on}(R_T) = \xi_{off}(R_T)$.

The CPL measurement may be further approximated by:

$$CPL = \frac{1}{(\sigma_a(\lambda_{on}) - \sigma_a(\lambda_{off}))} \left[ \frac{1}{2} \ln\left(\frac{E_1}{E_0} C_\rho\right) - \int_0^{R_T} (\overline{\kappa}(\lambda_{on}, R_T) - \overline{\kappa}(\lambda_{off}, R_T)) dR \right] \quad (6)$$

where it is assumed that there are no beam alignment problems.

In some cases, it is desired to measure a target fluid that is naturally present in the atmosphere. In such cases, the background concentration is typically measured and subtracted from the value calculated in equation (6). The CPL measurement for a target fluid that is naturally present may be approximated by:

$$CPL = \left[ \frac{1}{(\sigma_a(\lambda_{on}) - \sigma_a(\lambda_{off}))} \left( \frac{1}{2} \ln \frac{E_1}{E_0} C_\rho \right) - \int_o^{R_T} (\overline{\kappa}(\lambda_{on}, R_T) - \overline{\kappa}(\lambda_{off}, R_T)) dR \right] + N_b R_T \quad (7)$$

where $N_b$ is the background concentration.

Ideally, equation (6) or (7) may be used to detect a single target fluid. However, to account for non-ideal conditions several calibration parameters may be included. Then, the CPL may be approximated by:

$$CPL = \frac{C_{sys}}{2C_\sigma} \left( \ln\left(\frac{E_1}{E_0}\right) + \ln(C_\rho) + C_K' + C_{fit} \right) \quad (8)$$

where $$C_\sigma = (\sigma_a(\lambda_{on}) - \sigma_a(\lambda_{off})) \quad (9)$$

$$C_K = \ln(C_\rho) + C_K' \quad (10)$$

and where $$C_K' = - \int_o^{R_T} (\overline{\kappa}(\lambda_{on}, R_T) - \overline{\kappa}(\lambda_{off}, R_T)) dR \right]. \quad (11)$$

$C_\sigma$ represents the fluid absorption cross-section at each wavelength and is given in parts per million meter. $C_K'$ represents the effect of differences in atmospheric concentration length. $C_{sys}$ and $C_{fit}$ represent system parameters and units factors. These parameters are found experimentally as part of the system calibration.

It is understood that a differential reflectance algorithm may also be used by the present invention for detection of liquid targets provided the liquid has a detectable spectral signature.

According to an embodiment of the present invention, the system utilizes (1, . . . , N) on-line wavelengths and at least one off-line wavelength to detect desired target fluids. Accordingly, equation (8) may be computed for each energy ratio, i.e. $E_1/E_0, \ldots, E_N/E_0$.

According to an embodiment of the present invention, the system estimates the fluid absorption cross-section, $C_\sigma$. For example, for detecting natural gas, a gas cell may be provided within the detection system to adjust for shifts in transmitter output wavelengths. In general, an onboard monitoring system (FIG. 2) may be used to monitor shifts in transmitter output wavelengths for any fluid and to estimate the absorption cross-section.

Figure 2:
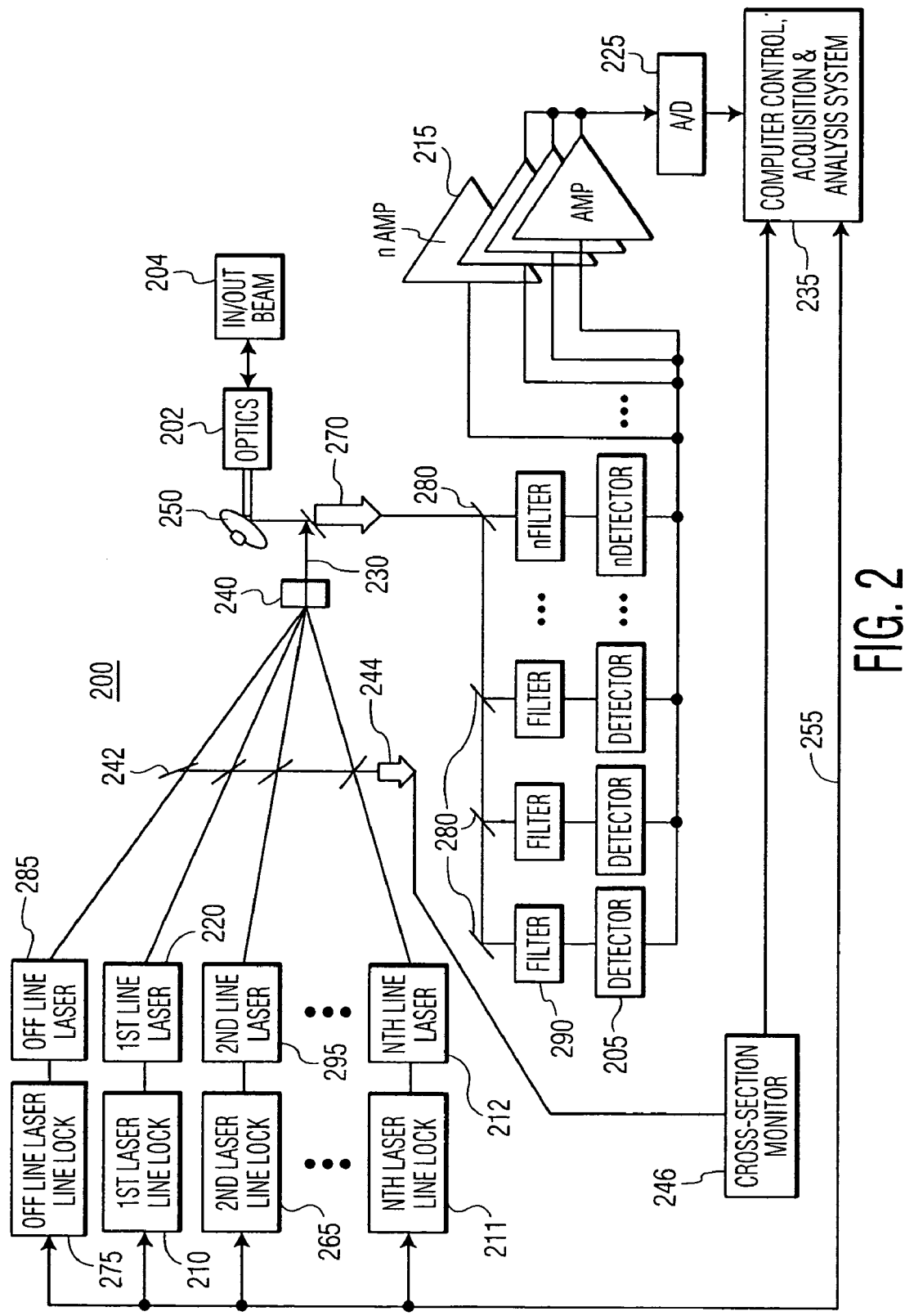
FIG. 2 is a functional block diagram illustrating an exemplary multi-line tunable DIAL laser fluid pipeline leak detection system, according to an embodiment of the present invention.

FIG. 2 is a functional block diagram illustrating an exemplary multi-line tunable DIAL laser system, generally designated as 200. As shown, multi-line tunable DIAL laser system 200 includes N+1 lasers of which N lasers are on-line lasers and one laser is an off-line laser. For example, first line laser 220 may be an on-line laser used for a first target trace fluid, second line laser 295 may be a second on-line laser used for a second target trace fluid, etc., and the Nth on-line laser 212 may be used for an Nth target trace fluid. Off-line laser 285 may be used for identifying a target-background. The N+1 line lasers may be, respectively, locked onto N+1 different wavelengths by line lock amplifiers 275, 210, 265, etc., and 211 using electronic control signals 255.

The on-line wavelengths may be selected close to the peak of a respective target fluid's optical absorption wavelength and the off-line wavelength may be selected near the wing of one of the target fluid's optical absorption wavelengths.

The outputs from the off-line laser and the N on-line lasers are provided as temporally spaced pulses that are combined into a large power pulse burst. The temporal spacing may be sufficiently close so that the pulses in the burst are transmitted to the same location. According to an exemplary embodiment, a single large power pulse burst is transmitted and received for each measurement location.

Although FIG. 2 illustrates a single off-line laser, it is contemplated that multiple off-line lasers may be used for removing different variability of system parameters. For example, surface covered type (background) reflectance variability may be removed.

System 200 includes an output energy monitoring system (not shown) within line lock amplifiers 275, 210, 265, etc., and 211 to monitor the output energy at each wavelength. The output from the output energy monitoring system is provided to computer control, acquisition and analysis system 235 and used to normalize the return energies of each respective wavelength, described further with respect to FIGS. 6 and 9.

The off-line and on-line laser beams 285, 220, 295, etc., and 212, respectively, are combined by holographic grating 240 to form combined laser beam 230. The combined laser beam 230 is transmitted by mirror 250 through optics 202 to form output laser beam 204. For the region of interest, target fluids in the atmosphere near the ground are sequentially scanned by output laser beam 204. At least a portion of output laser beam 204 may be reflected by the reflective surface as an input beam (also designated as 204), eventually becoming returned light 270.

The returned light 270 passes through a set of beam splitters 280 before encountering a set of filters 290. These set of filters are tuned, respectively, to pass each of the on-line and off-line wavelengths. A set of detectors 205 converts each of the filtered beams into a respective electronic signal. The electronic signals are amplified by amplifiers 215 and converted into a digital signal by analog to digital (A/D) converter 225. The digitized signal is processed and analyzed by computer control, acquisition and analysis system 235 to estimate the CPL for each target fluid wavelength, at each measurement location, using the on-line and off-line returned signals. Thus, target fluids are qualitatively identified and measured over a survey area based on the estimated CPLs.

System 200 includes cross-section monitor 246 which measures the fluid absorption cross-section $C_o$ (in ppm). Portions of the beam energies from on-line laser sources 220, 295, etc., and 212 and off-line laser source 285 are redirected by beam splitters 242 to cross-section monitor 246, shown as beam 244. In an exemplary embodiment, cross-section monitor 246 includes gas-cells (not shown) which contain a small quantity of the target fluids, such as natural gas, to be measured. The same gas cell containing the target fluid is also used to measure the cross-section absorption by the off-line wavelength. The gas cell may thus be used to measure a difference in absorption cross-section between each on-line wavelength and off-line wavelength (see equation 9). The differences between each on-line wavelength and off-line wavelength may be digitized by low rate A/D converters (not shown) and output to computer control, acquisition and analysis system 235. In an exemplary embodiment, the fluid absorption cross-section is performed in real-time in order to compensate for the stability of the on- and off-line laser wavelengths over a flight path.

Figure 3:
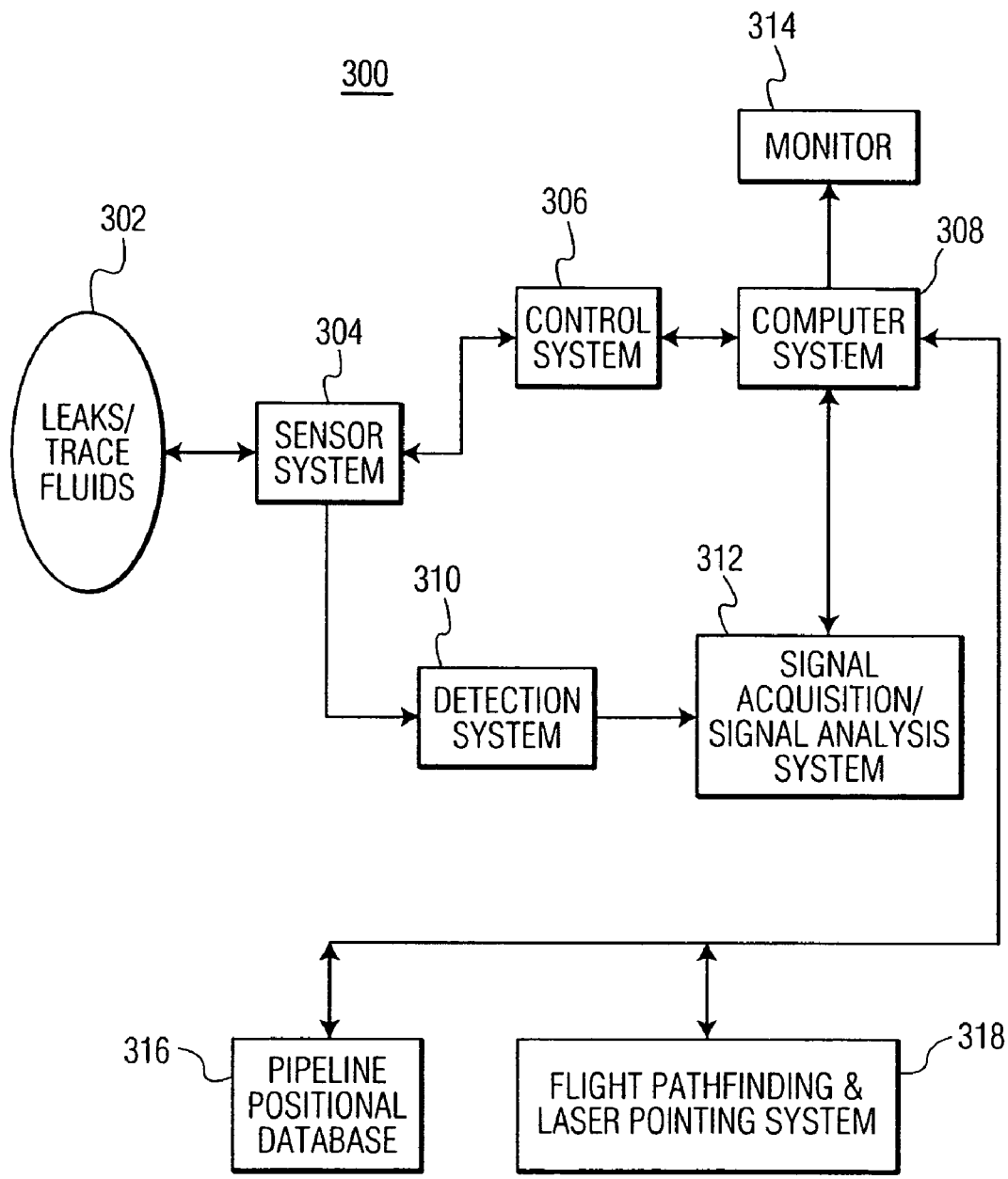
FIG. 3 is a high level functional block diagram illustrating an exemplary multi-line tunable DIAL laser fluid pipeline leak detection system according to an embodiment of the present invention.

FIG. 3 is a high level functional block diagram illustrating leak detection system 300, according to an embodiment of the present invention. A monitor 314 may be used to display various graphical user interfaces (GUI) that enable monitoring analysis of relevant process conditions for the leak detection system. Alternatively, the process may be automated such that use of monitor 314 may be optional. Computer system 308 sends control signals to control system 306 and receives feedback signals from control system 306. Computer system 308 accesses flight path data from pipeline positional database 316 and flight path-finding and laser pointing system 318 for guiding the aircraft along a planned flight path and accurately pointing the laser beams. Control system 306 controls sensor system 304 and communicates with the computer system to properly orient sensor system 304 in accordance with the guided positions of the aircraft.

Sensor system 304 transmits laser beams toward target fluids 302 and receives returned laser beams from target fluids 302. The returned light is provided to detection system 310 which detects and electronically conditions the returned signal at the off-line and on-line wavelengths. Detection system 310 digitizes the detected signal and provides the digitized signal to signal acquisition/signal analysis system 312. Although detection system 310 is illustrated as being a separate system, it is contemplated that detection system 310 may be part of sensor system 304. Signal acquisition/signal analysis system 312 estimates target fluid CPLs and generates two or three-dimensional target fluid maps.

Flight path-finding and laser pointing system 318 includes, on-board aircraft positional and motion measurement sensors, a GPS and an Inertial Measurement Unit (IMU).

Consumer-acquired pipeline positional data may be processed, filtered, normalized and stored in pipeline positional database 316. Pipeline positional database 316 may also process, filter and normalize the GPS and IMU positional data to predict an optimal flight path and update the pipeline positional database with the predicted flight path.

Figure 4A:
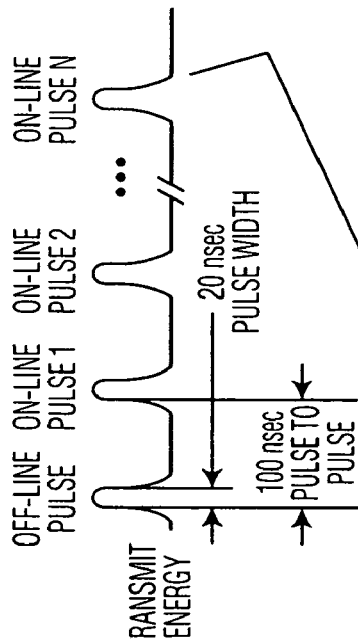
FIG. 4A is a schematic diagram illustrating an exemplary transmitted pulse burst transmitted from a DIAL system, according to an embodiment of the present invention.

Pulse bursts that are transmitted and received according to an aspect of the present invention are now described with respect to FIGS. 4A, 4B, 4C and 4D. FIG. 4A illustrates an exemplary pulse burst transmitted from a DIAL system, according to an embodiment of the present invention. The transmitted pulse burst includes N+1 pulses in the pulse burst, including an off-line pulse and N on-line pulses. The on-line pulses may represent spectral lines tuned to methane and ethane, for example. As shown in FIG. 4A, the pulse width is 20 nsec and there is a 100 nsec spacing between pulses. It is contemplated that the spacing between transmitted pulses may vary depending on the host platform (e.g. helicopter, fixed wing aircraft, stationary ground mount).

Figure 4B:
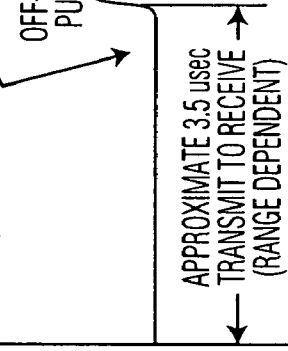
FIG. 4B is a schematic diagram illustrating an exemplary received pulse burst received by the DIAL system, according to an embodiment of the present invention.

FIG. 4B illustrates an exemplary pulse burst received by the DIAL system, based on the transmitted pulse burst shown in FIG. 4A. The received pulse train is delayed due to the two-way distance between the DIAL system and the target. Although shown as having a delay time of 3.5 μsec, it is understood that this is merely exemplary and dependent upon the target range. In this example, temporal separation of the return pulses may allow for temporal discrimination between the pulses.

FIG. 4B also illustrates that the amplitude of the received on-line pulses are reduced in comparison to the off-line pulse. This condition may occur if each of the respective target fluids are present. It is understood that not all target fluids may be present at a measurement location and the amplitude of each of the on-line pulses may differ.

Figure 4C:
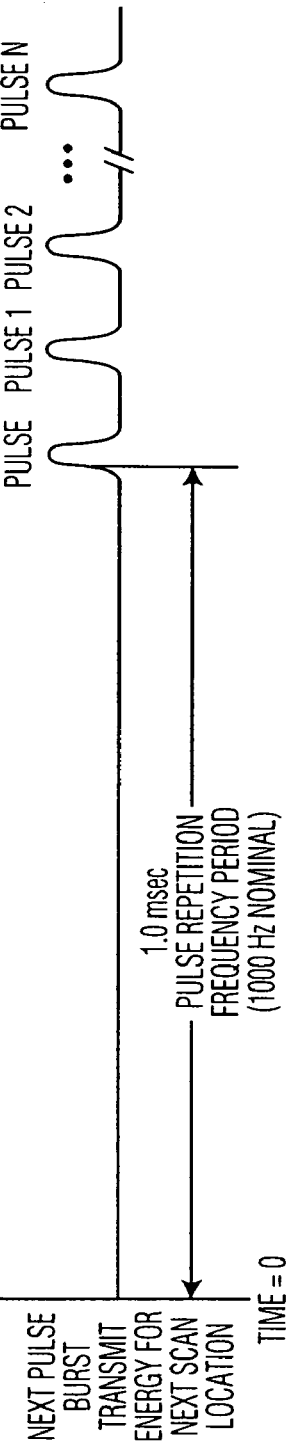
FIG. 4C is a schematic diagram illustrating an exemplary transmitted pulse burst transmitted from the DIAL system for a following measurement point, according to an embodiment of the present invention.

FIG. 4C illustrates the pulse repetition rate (PRF) of the transmitted pulse burst of FIG. 4A. The PRF is shown as 1 kHz, nominal (pulse repetition interval (PRI) of 1.0 msec). It is contemplated that the PRF may be between about 0-50 MHz, or higher.

Figure 4D:
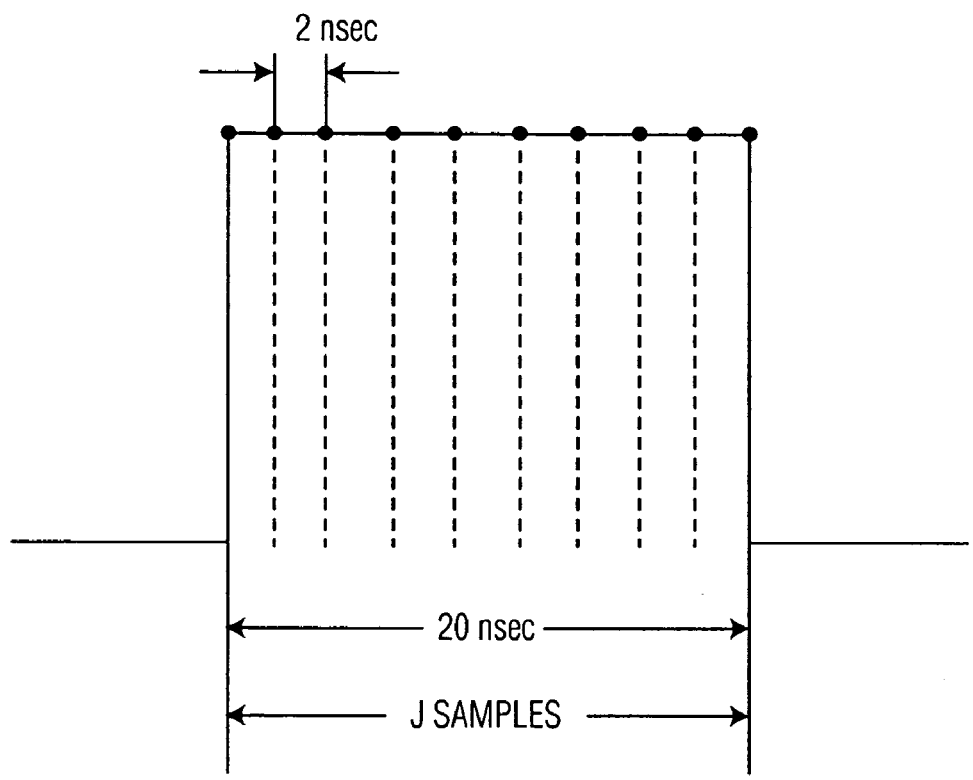
FIG. 4D is a schematic diagram illustrating one of the exemplary received pulses from a received pulse burst received by the DIAL system, according to an embodiment of the present invention.

FIG. 4D illustrates an exemplary ideal single pulse of the pulse burst received by the DIAL system. Although the pulse is shown as a rectangular pulse, in an exemplary embodiment, the pulse approximates a Poisson distribution. According to an exemplary embodiment, the pulse width is about 20 nsec. Each pulse is reconstructed from 10 samples, each sample of about 2 nsec width. This reconstruction is based on a sampling rate of 500 MHz. It is understood that a suitable pulse width may be reconstructed based on to the sampling rate of the system.

Figure 4E:
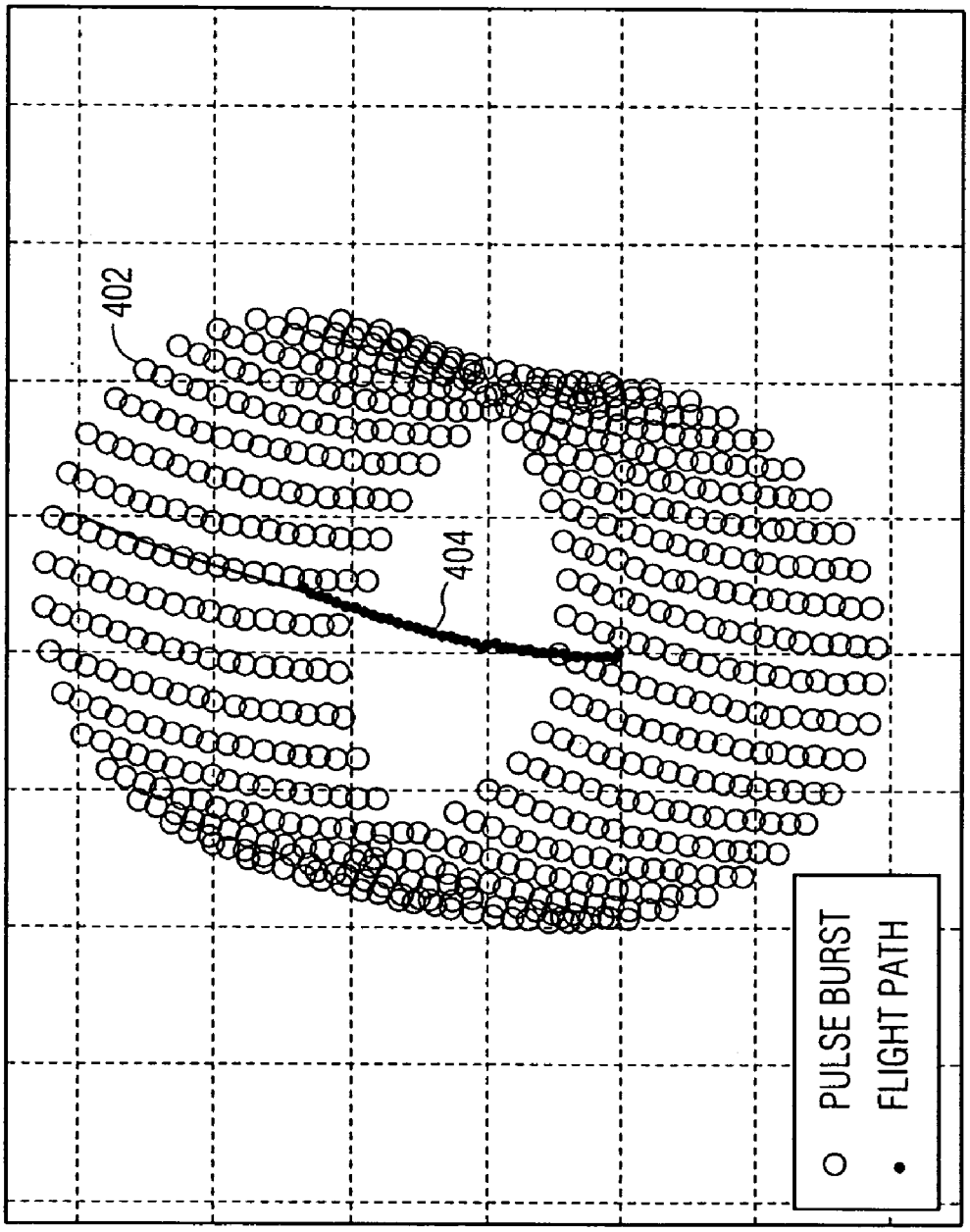
FIG. 4E is a schematic diagram illustrating variably distributed measurement points of an exemplary circular scan pattern according to an embodiment of the present invention.

FIG. 4E is a schematic diagram illustrating measurement points of an exemplary circular scan pattern of a transmitted beam from the DIAL system, according to an embodiment of the present invention. Measurement points 402 are taken in circles as the DIAL system moves along flight path 404. As may be seen, the measurement points form a non-linear pattern, which are bunched near the edges of the scan pattern. Although a circular scan pattern is illustrated in FIG. 4E, it is contemplated that other suitable scan patterns may be used.

For each measurement point 402, a single high energy pulse bundle (high pulse energy in each pulse, where the N+1 pulses are each at a different wavelength) is transmitted and received. A DIAL system typically transmits a plurality of low energy pulse bundles for each measurement point 402. The received pulses are typically averaged. This, however, requires long dwell times over the target measurement point and, therefore, reduces area coverage. The present invention, however, transmits a single high energy pulse bundle which allows for reduced dwell times over any single measurement point. The returned pulse bundle is reconstructed at the 500 MHz rate to provide 10 samples (for example) to reconstruct each pulse.

Figure 5:
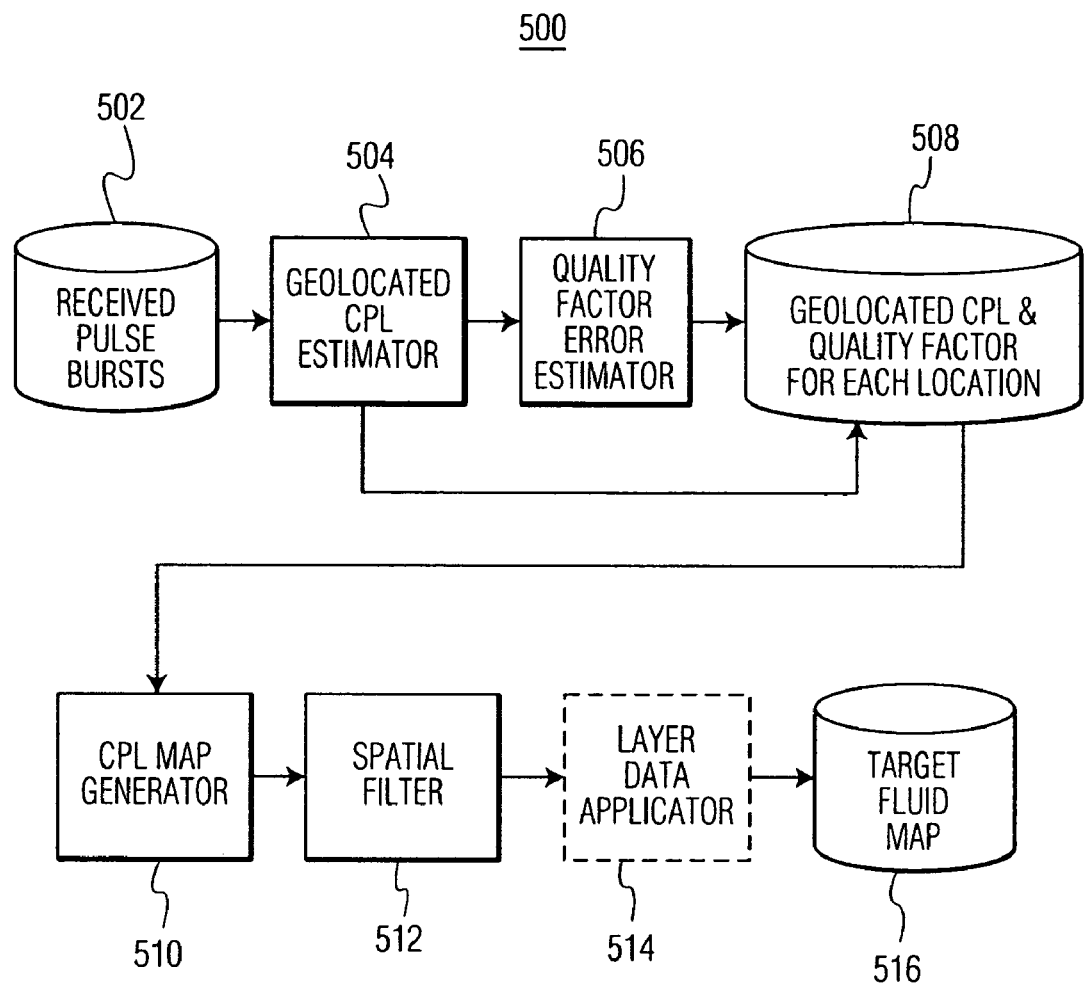
FIG. 5 is a functional block diagram illustrating an exemplary target fluid mapping system, according to an embodiment of the present invention.

FIG. 5 is a functional block diagram illustrating an exemplary CPL mapping system 500, according to an embodiment of the present invention. The received pulse bursts are stored in database 502. For example, signal acquisition/signal analysis system 312 (FIG. 3) acquires the received pulse bursts, such as shown in FIG. 4B, and provides them to database 502. Geolocated CPL estimator 504 retrieves the received pulse bursts from database 502 and provides geolocated estimates of the CPL for each on-line wavelength (described below with respect to FIGS. 6, 9 and 10).

The output of CPL estimator 504 is provided to quality factor error estimator 506. The quality factor error estimator estimates a data quality so that data points having poor SNR can be discarded. In the exemplary embodiment, CPL map generator 510 uses the estimated data quality factor to discard poor SNR quality data points.

The output of geolocated CPL estimator 504 and quality factor error estimator 506 are provided to database 508. The database stores the geolocated CPL and an associated quality factor for each geo-location.

CPL mapping system 500 includes CPL spatial map generator 510 for generating a CPL spatial map using the geolocated CPLs and associated quality factors retrieved from database 508. As shown, for example, in FIG. 4E, the measurement locations are variably distributed along a circular scan pattern. CPL spatial map generator 510 arranges the estimated CPLs by latitude and longitude. CPL spatial map generator 510 may also include elevation in the CPL estimates, where the elevation is altitude 140 (FIG. 1). Locations corresponding to a poor quality factor may be discarded from the CPL spatial map. The CPL spatial map generator 510 may use a standard geographical information system (GIS) file format and provide integration with other data layers.

CPL mapping system 500 also includes spatial filter subsystem 512 which receives the output of CPL map generator 510, i.e. the CPL spatial map. The CPL spatial map may include noise due to processing of a single pulse burst for each measurement location. Noise may also be introduced into the CPL spatial map by interference due to spectral surface reflectivity fluctuations. Spatial filter 512 processes the CPL spatial map to reduce signal fluctuations due to the spectral surface reflectivity and clutter. In an exemplary embodiment, spatial filter subsystem 512 uses a Gaussian smoothing operator (a two-dimensional convolution operator). Other smoothing filters may also be used.

System 500 may include a layer data applicator 514 which receives the output from spatial filter subsystem 512 and applies ancillary data to augment the CPL map. The ancillary data may include digital photography, land use maps, pipeline location information, pipeline access information, and population information. The ancillary information may be stored in pipeline positional database 316 (FIG. 3). The ancillary data may be integrated with the spatially filtered CPL map using graphical GIS techniques. The geolocation of the ancillary data may be performed, for example, by 3 band passive imagery taken from an on-board camera in airplane 110 (FIG. 1). The spatially filtered CPL map and the ancillary data form the two-dimensional or three-dimensional target fluid map, which is stored in database 516. The output of database 516 may be provided to monitor 314 (FIG. 3). Further analysis of the target fluid map provides an estimate of the plume volume and/or leak rate.

Figure 6:
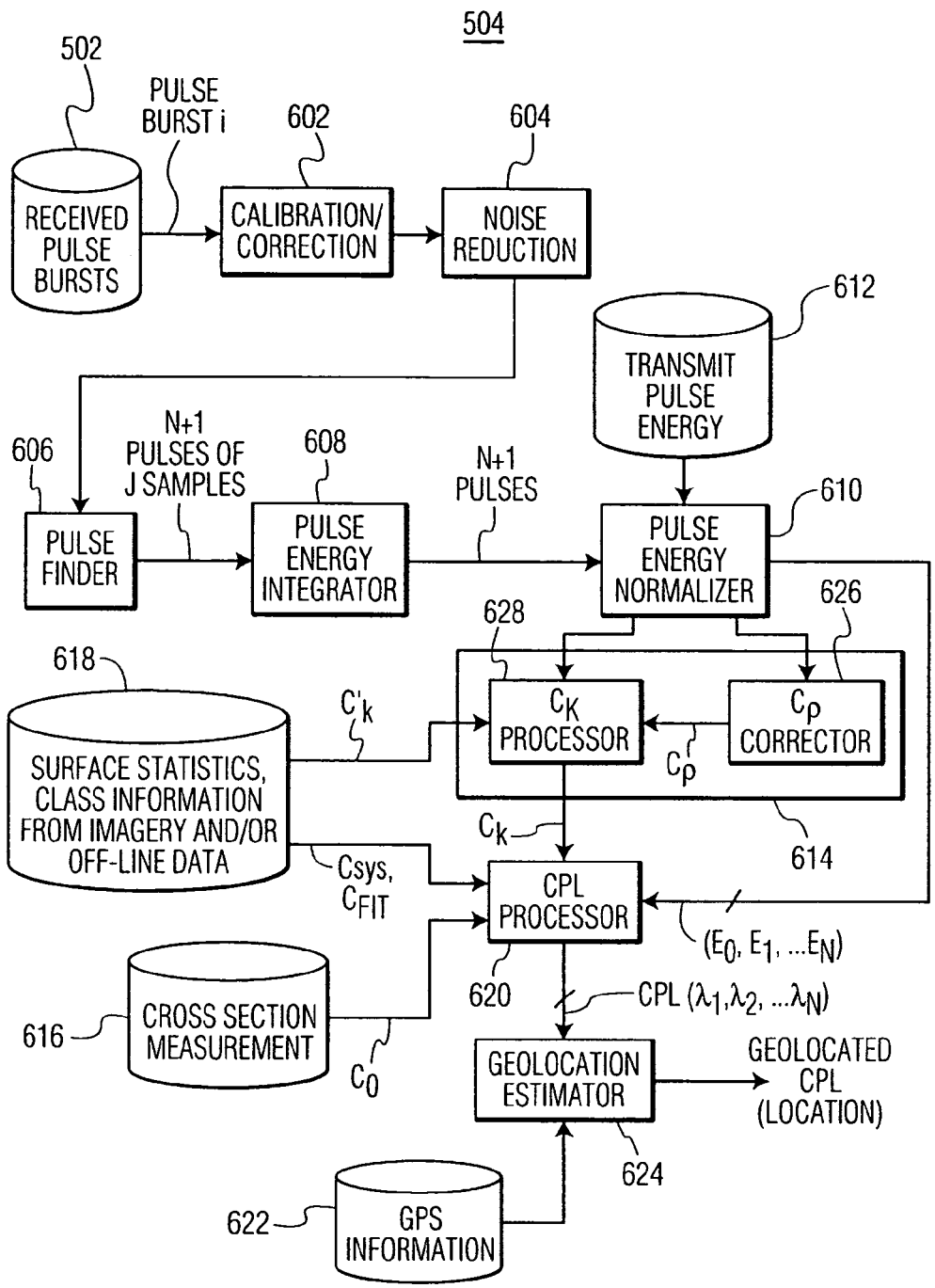
FIG. 6 is a functional block diagram illustrating an exemplary geolocated CPL estimator, according to an embodiment of the present invention.

FIG. 6 is a functional block diagram illustrating an exemplary geolocated CPL estimator 504, according to an embodiment of the present invention. CPL estimator 504 retrieves a pulse burst from database 502 corresponding to location i and provides the pulse burst to calibration/correction subsystem 602. Calibration corrections based on known system properties are implemented to correctly scale the measured data. Calibration corrections, for example, include corrections for atmospheric and surface reflectivity effects and corrections for characteristics of the optical system.

Noise reduction subsystem 604 receives the output from calibration/correction subsystem 602 and applies an average or other type of filter to remove salt-pepper (spike) or other type noise from the data.

Pulse finder 606 receives the output from noise reduction subsystem 604 and determines the location of each of the pulses in the pulse burst. For example, pulse locations within the pulse burst shown in FIG. 4B are determined. The pulse locations are associated with the pulse bursts corresponding to the off-line and on-line pulses, i.e. wavelengths ($\lambda_0, \lambda_1, \ldots, \lambda_N$). Each pulse, as shown in FIG. 4D, includes a plurality of J samples. Pulse finder 606 determines a temporal inter-pulse separation between the series of received pulses, for example, based upon the pulse separation of the transmitted pulse burst (FIG. 4A). A first pulse in the received pulse burst may be determined, for example, by estimating a first maximum peak level that corresponds to the first return pulse in the pulse burst. Alternatively, the received pulse burst may be convolved with a predetermined filter having characteristics associated with the temporal inter-pulse separation to provide a location, i.e. sample, corresponding to the peak of the first pulse return. The temporal inter-pulse separation may then be used to estimate the location of the next pulse peak. The remaining peaks in the series may be similarly determined. Pulse finder 606 determines the locations for the start and end of each received pulse where each pulse has a width of J samples. U.S. patent application Ser. No. 11/156,150 filed on Jun. 17, 2005 to Lopez et al. entitled PULSE FINDING APPARATUS AND METHOD, describes a method for detecting pulses in a pulse burst.

Pulse energy integrator 608 receives the output from pulse finder 606 and calculates the total energy in each located pulse. As shown in FIG. 4D, each pulse includes J samples. The total energy in each pulse is determined by integrating the received pulse burst over the J samples.

Pulse energy normalizer 610 receives the pulse energy associated with the N+1 pulses, including the off-line pulse, and normalizes the energies relative to the transmitted pulses. Pulse energy normalizer 610 retrieves output pulse burst energies from database 612 corresponding to each of the received N+1 pulse energies. The transmitted pulse energies are computed and stored in database 612 by output energy monitoring system (part of line-lock amplifiers 275, 210, 265, etc., and 211 (FIG. 2)). The total energy in each pulse of a received pulse burst may thus be normalized as:

$$E_n = \frac{E_n^R}{E_n^T} \quad (12)$$

where R represents the received pulse energy, T represents the transmitted pulse energy and n represents the corresponding pulse from among the N+1 pulses. The output of pulse energy normalizer 610 is provided to CPL processor 620.

$C_k$ estimator 614 estimates differences in atmospheric concentration $C_k$. $C_k$ estimator 614 also corrects for variations in $C_\rho$ using $C_\rho$ corrector 626 by determining a region of like reflectivity (ROLR) proximate to pulse burst location i. The ROLRs for a survey area are estimated from the return energy statistics, including a covariance between the return wavelengths, i.e. ($\lambda_0, \lambda_1, \ldots, \lambda_N$). $C_k$ estimator 614 includes $C_k$ processor 628 which combines $C_\rho$ retrieved from $C_\rho$ corrector 626 and C'$_k$ retrieved from database 618 according to equation (10). C$_\rho$ correction and C$_k$ estimation is discussed further below with respect to FIGS. 10A and 10B.

CPL processor 620 receives the normalized energies from pulse energy normalizer 610, as well as the estimated and reflectivity corrected C$_k$ from C$_k$ estimator 614. CPL processor 620 also retrieves cross-section measurements, C$_\sigma$, from database 616 and C$_{sys}$ and C$_{fit}$ from database 618. Using equation (8), the normalized energies, E$_i$, together with C$_k$, C$_\sigma$, C$_{sys}$ and C$_{fit}$ are used to estimate the CPL, for each on-line wavelength, i.e. target fluid.

The survey area may be classified into reflectivity classes. Database 618 stores surface statistics and class information corresponding to ROLRs from is imagery and/or ground based data. In an exemplary embodiment, C'$_k$ is determined during calibration of the system and stored in database 618. Database 618 stores C$_{fit}$ and C$_{sys}$ which are calibrated from ground-based measurements.

Geolocation estimator 624 retrieves GPS information from database 622 and estimates a geolocation for each measurement location i. GPS information may be provided to database 622 from flight pathfinding and laser pointing system 318 (FIG. 3). GPS information is used to assign latitude, longitude and elevation to each measurement location.

Figure 7:
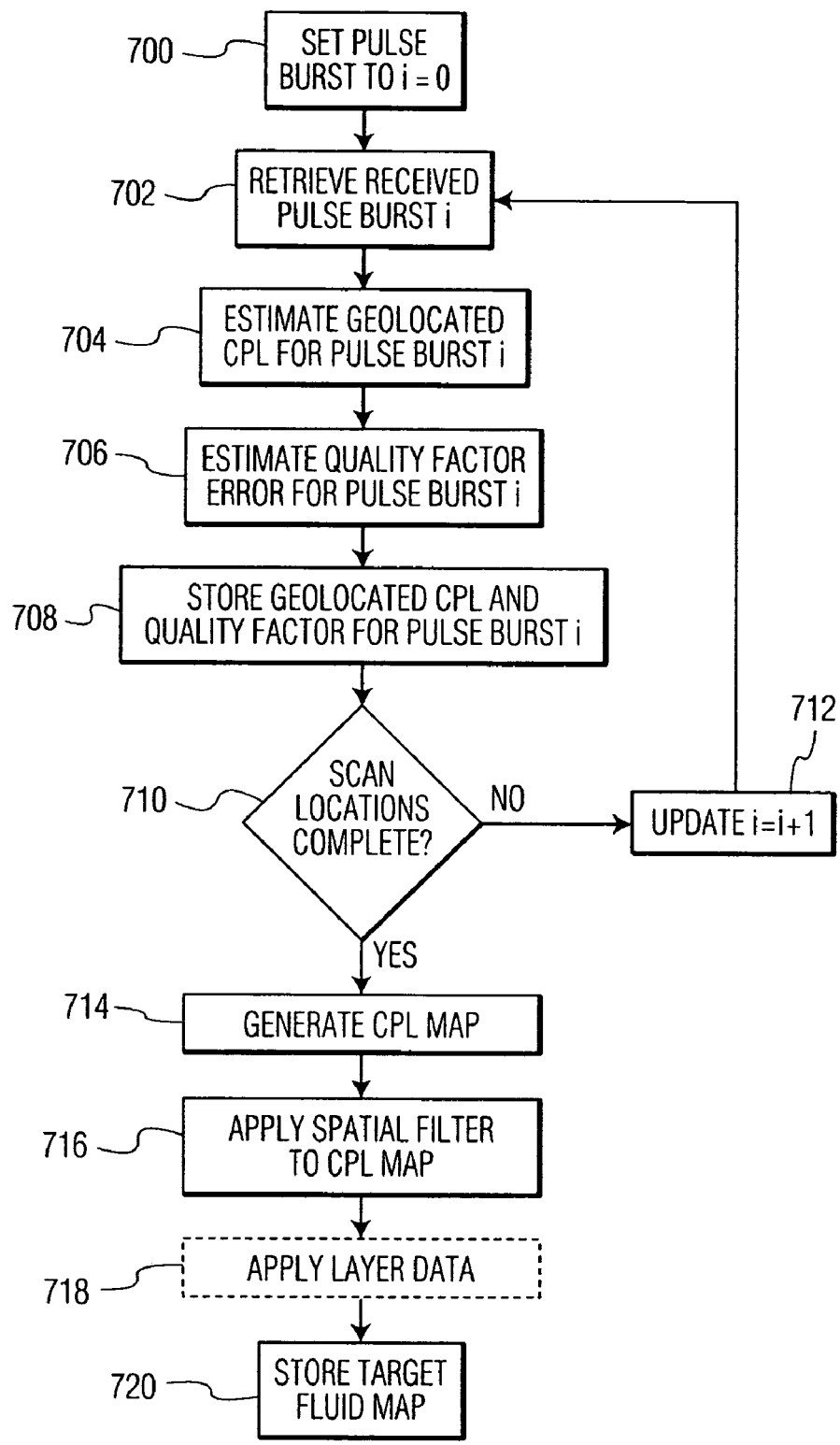
FIG. 7 is a flow diagram illustrating an exemplary method for converting received pulse bursts into a target fluid map, according to an embodiment of the present invention.

FIG. 7 is a flow chart illustrating an exemplary method for converting received pulse bursts into a target fluid map, according to an embodiment of the present invention. In step 700, a received pulse burst location is set to zero, corresponding to a first measurement location. In step 702, the next received pulse burst, corresponding to location i, is retrieved, from database 502 (FIG. 5). In step 704, a geolocated CPL is estimated for the retrieved pulse burst corresponding to location i, using geolocated CPL estimator 504 (FIG. 5). In step 706, a quality factor is estimated for the retrieved pulse burst corresponding to location i, using quality factor error estimator 506. In step 708, the geolocated CPL and quality factor for the retrieved pulse burst corresponding to location i are stored in database 508 (FIG. 5).

In step 710, a decision is made whether all of the scan locations are complete, i.e. whether all of the measurement locations have been accounted for. If the scan locations are complete, step 710 proceeds to step 714. Otherwise, step 710 proceeds to step 712.

In step 712, the measurement location is updated by incrementing a counter. Step 712 branches back to step 702 in order to process the next scan location. This process continues until all data is converted to CPL data points. Each CPL data point for each on-line wavelength represents the amount of a corresponding target fluid present at a specific measurement location.

Referring back to step 706, an exemplary method for estimating the quality factor error is described. Based on a first-order error propagation, a CPL variance may be calculated by:

$$CPL_{var} = \left[\frac{1}{2C_\sigma}\right]^2 \left\{ \left[\frac{\sigma_{off}^{2R}}{(E_{off}^R)^2}\right] + \left[\frac{\sigma_{on}^{2R}}{(E_{on}^R)^2}\right] + \left[\frac{\sigma_{off}^{2T}}{(E_{off}^T)^2}\right] + \left[\frac{\sigma_{on}^{2T}}{(E_{on}^T)^2}\right] + \text{CONVARIANCE\_TERMS} \right\}, \quad (13)$$

where $\sigma^2$ represents a variance, E represents pulse power, the superscripts T and R represents the respective transmitted and return pulses and the subscripts on and off represent the respective on-line and off-line wavelengths.

Because $(\sigma/E)^2$ is equivalent to 1/SNR, equation (13) may be written as:

$$CPL_{var} = \left[\frac{1}{2C_\sigma}\right]^2 \left\{ \left[\frac{1}{SNR_{off}^R}\right]^2 + \left[\frac{1}{SNR_{on}^R}\right]^2 + \left[\frac{1}{SNR_{off}^T}\right]^2 + \left[\frac{1}{SNR_{on}^T}\right]^2 + \text{CONVARIANCE\_TERMS} \right\} \quad (13a)$$

where the subscripts and superscripts are the same as for equation 13.

Because $$\left[\frac{1}{SNR_{off}^T}\right]^2, \left[\frac{1}{SNR_{off}^T}\right]^2$$

and COVARIANCE_TERMS are relatively very small, the CPL variance at each point can be estimated by:

$$CPL_{var}\left[\frac{1}{2\Delta C_\sigma}\right]^2 \left\{ \left[\frac{1}{SNR_{off}^R}\right]^2 + \left[\frac{1}{SNR_{on}^R}\right]^2 \right\} \quad (14)$$

and the CPL standard deviation, CPL$_{sd}$, can be estimated by:

$$(CPL_{sd}) = \sqrt{CPL_{var}} = \left[\frac{1}{2C_\sigma}\right]\sqrt{\left\{\left[\frac{1}{SNR_{off}^R}\right]^2 + \left[\frac{1}{SNR_{on}^R}\right]^2\right\}} \quad (15)$$

In practice CPL$_{sd}$ may be estimated from the transmitted on-line and off-line laser pulse energy, the returned off-line energy, and the measured cross section as shown in equation 15a:

$$CPL_{sd} = \left[\frac{1}{2C_\sigma}\right]\sqrt{\left[\frac{\sigma_{off}^{2R}}{(E_{off}^R)^2}\right] + \left[\frac{\sigma_{on}^{2R}}{(E_{on}^R)^2}\right]}. \quad (15a)$$

The quality factor (QF) is related to CPL$_{sd}$ by $$QF = 3 \times CPL_{sd} < \text{threshold} \quad (16)$$

Figure 8:
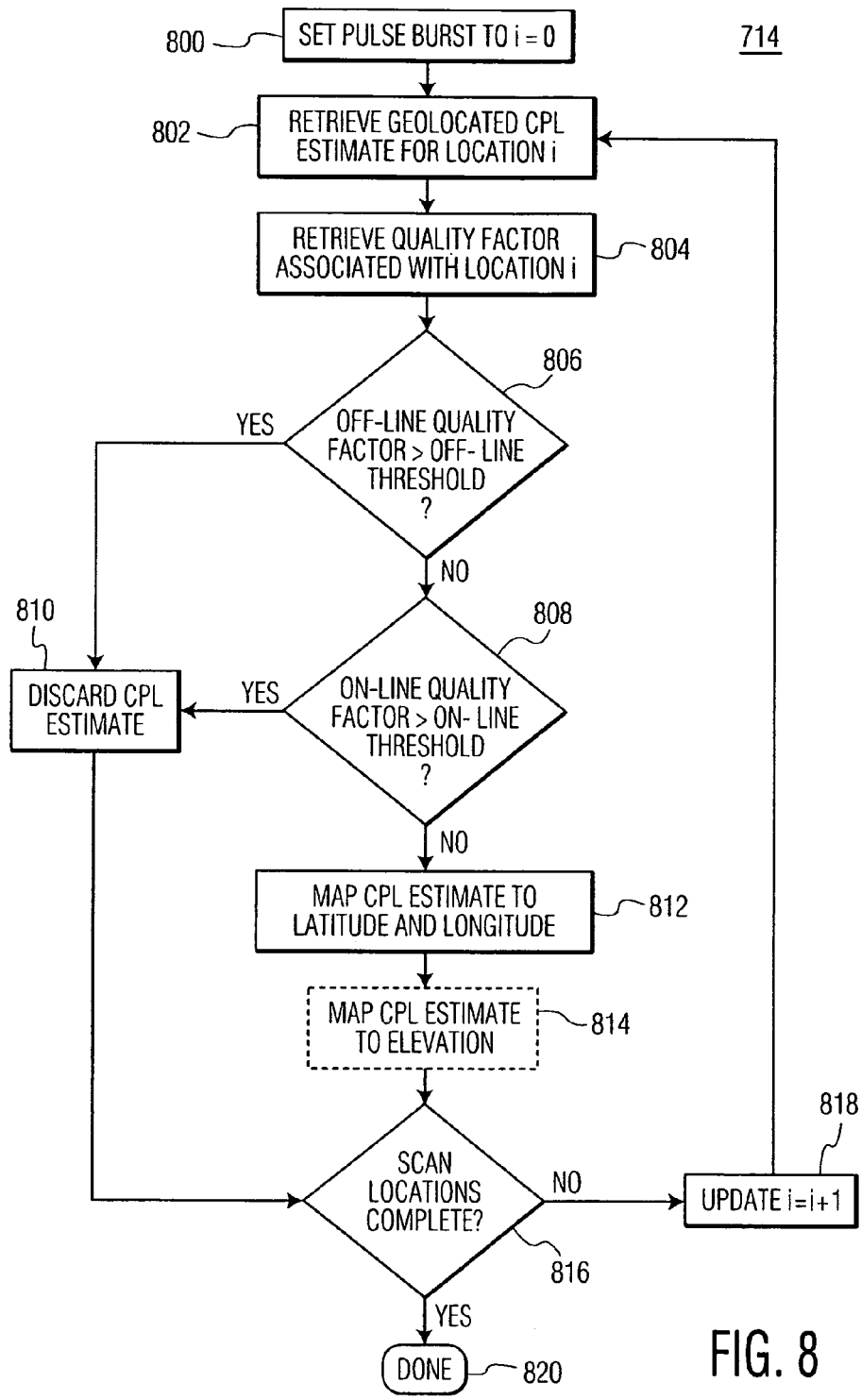
FIG. 8 is a flow diagram illustrating an exemplary method for generating a CPL spatial map from geolocated CPL estimates and a quality factor, according to an embodiment of the present invention.

The QF of equation 16 is compared against a predetermined threshold such that if the QF is larger than the threshold, the CPL estimate is discarded from the CPL map generated in step 714 (described further below with respect to FIG. 8). The threshold may be determined based on statistics of the collected data for the geographic location.

In step 714, a CPL map is generated, using CPL map generator 510 (FIG. 5). This step now described with respect to FIG. 8. As shown, step 800 sets a pulse burst location to zero, corresponding to the first measurement location. In step 802, the geolocated CPL estimate corresponding to location i is retrieved from database 508 (FIG. 5). In step 804, the associated quality factor corresponding to location i is retrieved from database 508 (FIG. 5).

In step 806, a decision is made whether the off-line quality factor is greater than a predetermined off-line threshold of equation (16). If the off-line quality factor is greater than the off-line threshold, step 806 branches to step 810. If the off-line quality factor is less than or equal to the off-line threshold, step 806 branches to step 808.

In step 810, the CPL estimate is discarded for that measurement location. Step 810 then branches to step 816.

In step 808, a decision is made whether the on-line quality factor is greater than a predetermined on-line threshold. In an exemplary embodiment, each of the on-line quality factors for the N on-line wavelengths are compared to the on-line threshold. If the on-line quality factor is less than or equal to the on-line threshold, step 808 branches to step 812. If, on the other hand, the on-line quality factor is greater than the on-line threshold, step 808 branches to step 810, and the CPL estimate is discarded for that measurement location. Step 810 then branches to step 816.

In step 812, the CPL estimate is mapped to latitude and longitude using the geolocation obtained in step 704 (FIG. 7). If included in the method, the CPL estimate is mapped to an elevation by step 814.

In step 816, a decision is made whether all of the scan locations are complete, i.e. whether all of the measurement locations are accounted for. If the scan locations are complete, step 816 proceeds to step 820 and the process is complete. Otherwise, step 816 proceeds to step 818. In step 818 the measurement location is updated by incrementing a counter. Step 818 proceeds to step 802 and continues the method. This method is repeated until all the geolocated CPL estimates are mapped as a CPL spatial map.

It is contemplated that the off-line threshold and the on-line threshold may be set to different levels, to account for the low energy on-line returns compared to the off-line returns. It is further contemplated that a different on-line threshold may be applied for each expected target fluid if the target fluid returns are known to exhibit various levels of return energy.

Referring back to FIG. 7, in step 716, a spatial filter is applied to the CPL map, using spatial filter 512 (FIG. 5). In an exemplary embodiment, a region is chosen around each measurement location and Gaussian smoothing is performed using convolution methods. Alternatively, filtering may be performed temporally with a one dimensional filter acting on the measurements in the order in which they are collected. In a further embodiment, a sliding convolution may be performed by a sub-set of the CPL map over the collection area. This method is faster but less accurate than Gaussian smoothing. Performing sliding convolution may also affect gridding of the data.

In alternate step 718, ancillary layer data may be applied to the spatially filtered CPL map, using layer data applicator 514. In step 720, a target fluid map, formed by the spatially filtered CPL map, in step 716, or by ancillary layer data stored in database 516 (FIG. 5).

Figure 9:
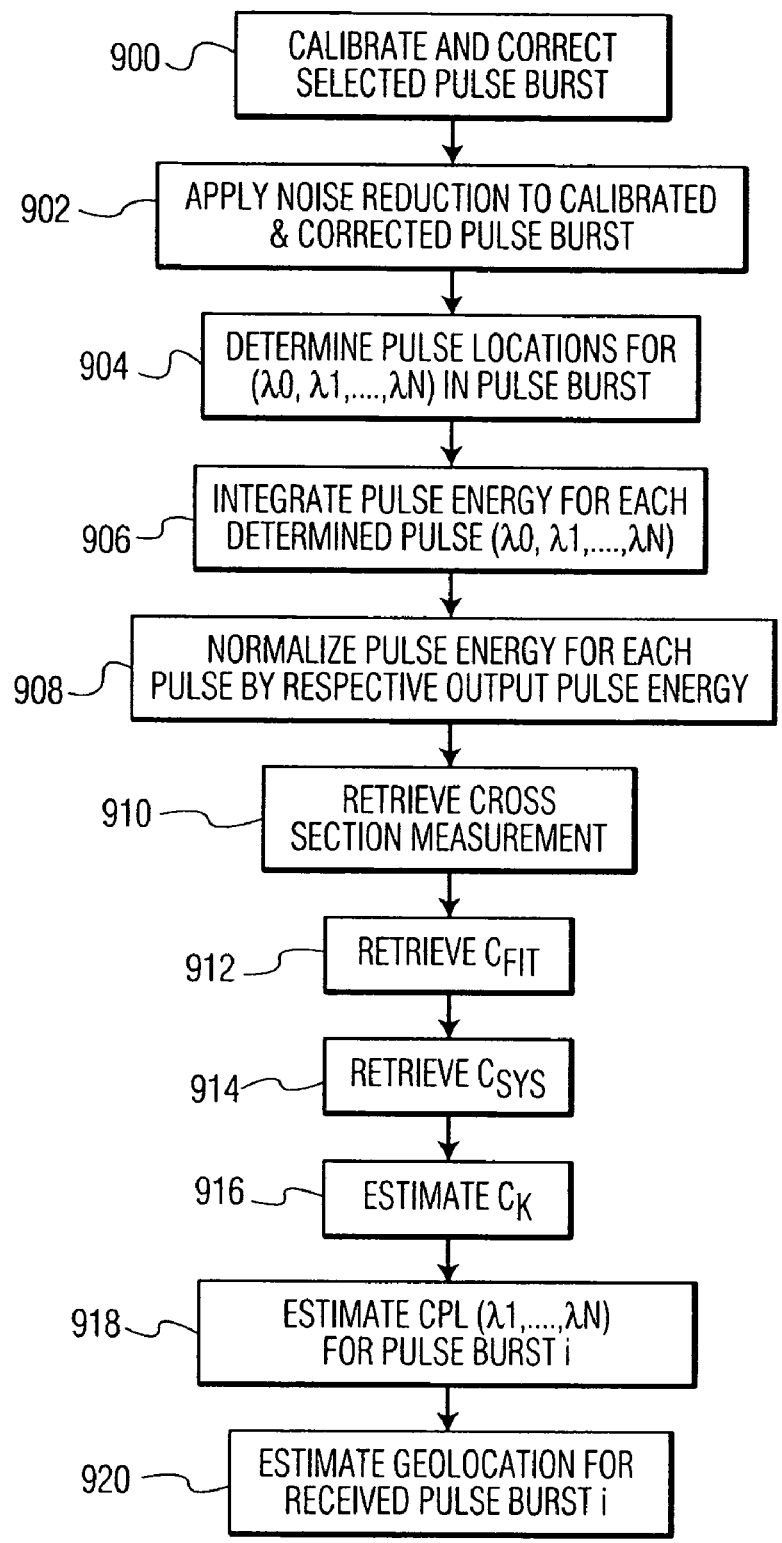
FIG. 9 is a flow diagram illustrating an exemplary method for converting a received pulse burst into a geolocated CPL estimate, according to an embodiment of the present invention.

FIG. 9 is a flow diagram illustrating in more detail, step 704 (FIG. 7) for converting a received pulse burst into a geolocated CPL estimate, according to an embodiment of the present invention. In step 900, the retrieved pulse burst, corresponding to measurement location i, is calibrated and corrected. In step 902, noise reduction is performed on the corrected pulse burst, for example, by using noise reduction subsystem 604 (FIG. 6).

It is contemplated that steps 900 and 902 may be performed for each measurement location and stored in database 502 for further CPL estimation. Thus, processing of step 704 begins with calibrated/corrected and noise reduced pulse bursts, associated with location i.

In step 904, pulse locations for each pulse in the received pulse burst are determined, for example, using pulse finder 606 (FIG. 6). The received pulse burst is sampled at a high rate to construct each return pulse with J samples. In step 906, the energy for each pulse is computed by integrating the pulse energy over the J samples, using pulse energy integrator 608 (FIG. 6). The integrated energy represents the total energy in each pulse return. In step 908, the pulse energies for each on-line and off-line returns are normalized by the respective transmitted pulse energy, using pulse energy normalizer 610 (FIG. 6).

In step 910, cross-section measurements, $C_\sigma$, are retrieved, from database 616 (FIG. 6). In step 912, $C_{fit}$ is retrieved. In step 914, $C_{sys}$ is retrieved. $C_{fit}$ and $C_{sys}$ are retrieved from database 618 (FIG. 6). In step 916, $C_k$ is estimated and $C_\rho$ is normalized, using $C_k$ estimator 614 (described further below with respect to FIG. 10). In step 918, a CPL is estimated for each on-line wavelength ($\lambda_1, \ldots, \lambda_N$) corresponding to a respective target fluid. The CPL is estimated using $C_\sigma$ (step 910), $C_{fit}$ (step 912), $C_{sys}$ (step 914) and $C_k$ (step 916) based on the normalized energies computed in step 908. CPL processor 620 (FIG. 6) is used to estimate the CPL for each on-line wavelength.

In step 920, the geolocation associated with each estimated CPL is determined using geolocation estimator 624 (FIG. 6). It is contemplated that step 920 may be performed after step 904. In this manner, a CPL corresponding to each target fluid is provided with a geolocation for mapping of the CPLs.

Figure 10A:
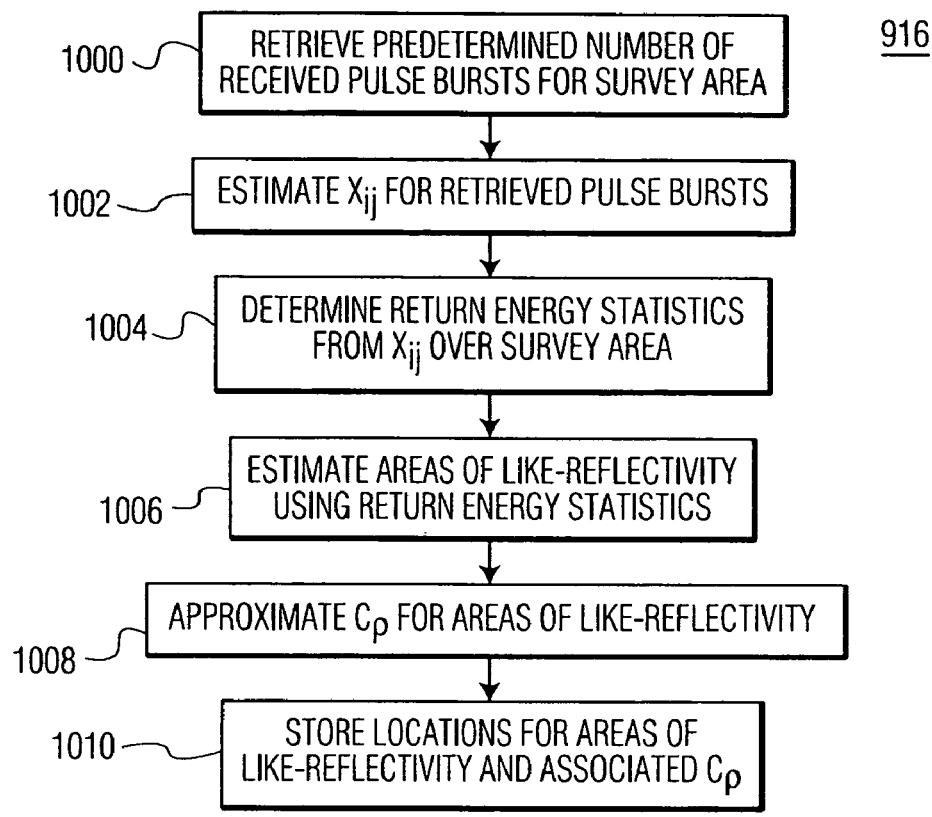
FIG. 10A is a flow diagram illustrating an exemplary method for correcting for a reflectivity ratio, according to an embodiment of the present invention.
Figure 10B:
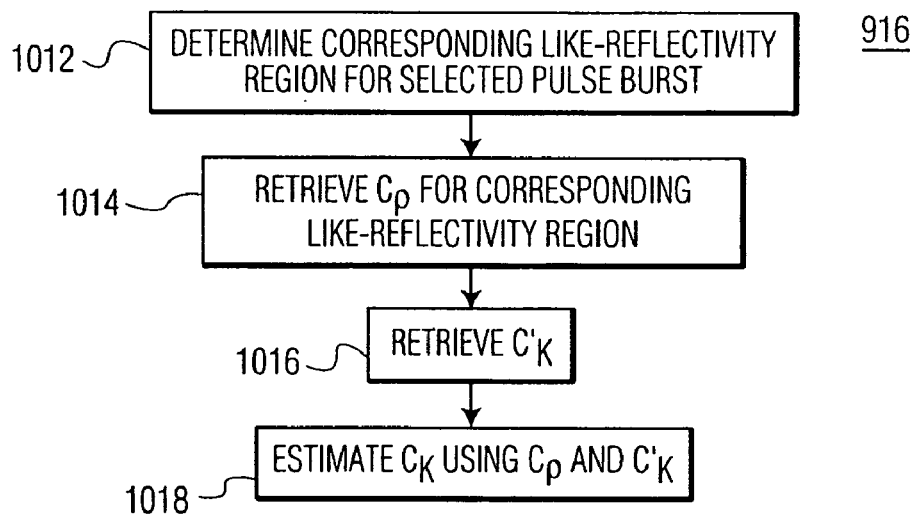
FIG. 10B is a flow diagram illustrating an exemplary method for estimating an atmospheric concentration length using the corrected reflectivity ratio, according to an embodiment of the present invention.

FIGS. 10A and 10B are flow diagrams illustrating in more detail, step 916 (FIG. 9) for estimating atmospheric concentration length, $C_k$, including correcting $C_\rho$, according to an embodiment of the present invention. FIG. 10A illustrates an exemplary method for estimating ROLR's and for correcting $C_\rho$, such as with $C_\rho$ corrector 626. In general, $C_\rho$ varies from surface to surface as well as for each on-line and off-line wavelength. ROLR's may be determined and the statistics of the region may be used to represent the reflectivity for that region.

In step 1000, a predetermined number of received pulse bursts for the survey area are selected. In step 1002, the return energies for the on-line and off-line returns are measured. As shown by equation (1), the return energy $E(\lambda,t)$ is proportional to $\rho(\lambda)$. The statistics of the reflectivity can thus be inferred by observing the change in the return energies for a ROLR.

The received energy, Equation (1), may be converted to signal electrons at the detector as:

$$X_{ij} = \left( \frac{g\eta}{bg'\eta'} \underbrace{\frac{\tau_d A_o}{\pi} \frac{T_{air}^2}{R_T^2} \xi_j \xi(R_T) \rho_j}_{\text{nonfluctuating}} \right) + \underbrace{(n_{ij})}_{\text{fluctuating}} \qquad (17)$$

where $X_{ij}$ represents the discrete received energy for measurement location i and wavelength j, g represents the gain of the receiver, g' represents gain of the power monitor, $\eta$ represents receiver quantum efficiency, $\eta'$ represents power monitor quantum efficiency, b is a normalization factor used to match the magnitude of the received and power monitor energies, rd represents the detector integration time, $A_o$ is a parameter that describes the optical system, $T_{air}^2$ represents the two-way transmission through the atmosphere, and $n_{ij}$ represents an added noise term. As in equation (1), $R_T$ represents the range or distance to the surface, $\tau_j$ and $\xi(R_T)$ represent the spectral response of the optical system and the receiver/laser geometric form factor and $\rho_j$ represents reflectivity at wavelength j.

In step 1004, return energy statistics are determined from equation (17). In an exemplary embodiment, the return energy statistics include a mean and covariance that are determined using the received pulse bursts. Equation 17 represents the return energy divided by the measured outgoing energy per pulse.

Equation (17) can generally be represented by:

$$X_{ij} = G_j + n_{ij} \quad (18)$$

where $G_j$ represents a non-fluctuating portion and $n_{ij}$ represents a fluctuating portion of the signal.

The mean, $\hat{G}_j$, may be estimated by:

$$\hat{G}_j = \frac{1}{M} \sum_{i=1}^{M} X_{ij} \quad (19)$$

where M represents a total number of measurement points.

The covariance, $\hat{\Lambda}_{jj'}$, may be estimated by:

$$\hat{\Lambda}_{jj'} = \frac{1}{M} \sum_{i=1}^{M} (X_{ij} - \hat{G}_j)(X_{ij'} - \hat{G}_{j'}) \quad (20)$$

The estimated covariance of equation (20) uses computations between target fluid wavelengths where j and j' represent target fluid wavelengths including j≠j'.

In step 1006, the ROLR's are estimated using the covariance of equation (20). In an exemplary embodiment, the region boundaries may be directly determined from equation (20) by grouping regions of similar covariance. In an alternate embodiment, a maximum likelihood estimator may be used estimate ROLR boundaries.

In step 1008, $C_\rho$ is estimated for each ROLR. In an exemplary embodiment, $C_\rho$ is estimated by normalizing the associated mean of the reflectivity for each on-line wavelength by the mean of the reflectivity for the off-line wavelength as:

$$C_\rho = \frac{\hat{G}_{on}}{\hat{G}_{off}} \quad (21)$$

In an alternate embodiment, where a maximum likelihood estimator is used, $C_\rho$ is estimated according to equation (21a) as:

$$C_{\rho i,j} = \frac{\hat{G}_i}{\hat{G}_j} \quad (21a)$$

where i and j both represent the on-line and off-line wavelengths and i≠j. For example, for three wavelengths (such as two on-line and one off-line wavelength), six ratios are estimated.

In step 1010, the ROLRs and associated Cρ's for each on-line wavelength are stored in $C_\rho$ corrector 626, such as in a look up table (LUT).

FIG. 10B illustrates the process of estimating $C_k$ using the corrected reflectivity ratio Cρ. In step 1012, a corresponding ROLR for a received pulse burst, i.e. proximate to location i, is determined from the stored ROLR's. In step 1014, the Cρ's corresponding to the ROLR are retrieved, such as from the Cρ corrector 626.

In step 1016, $C_k'$ is retrieved from database 618 and, as discussed above, is typically determined during system calibration. In step 1018, $C_k$ is then processed, for example using $C_k$ processor 628, according to equation (10) by combining $C_k'$ and Cρ for the respective target fluid wavelengths.

Although the invention has been described as apparatus and a method, it is contemplated that it may be practiced by a computer configured to perform the method or by computer program instructions embodied in a computer-readable carrier such as an integrated circuit, a memory card, a magnetic or optical disk or an audio-frequency, radio-frequency or optical carrier wave.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A method for obtaining a target fluid map of a survey area using a differential absorption LIDAR (DIAL) system, the method comprising the steps of:
    a) transmitting a plurality of pulse bursts toward the survey area, each transmitted pulse burst including an off-line pulse and at least one on-line pulse;
    b) receiving a plurality of pulse bursts from the survey area, each received pulse burst associated with a measurement point;
    c) determining, for each measurement point:
        (i) a concentration path length (CPL) corresponding to a respective on-line pulse,
        (ii) a spatial location associated with the CPL determined in step (i), and
        (iii) an error associated with the CPL determined in step (i); and
    d) arranging the CPL for each of the measurement points within the survey area to form the target fluid map.

2. The method according to claim 1, wherein step (d) includes arranging each CPL using the corresponding spatial location determined in step (ii).

3. The method according to claim 1, wherein the target fluid map includes noise artifacts, and the method further includes the step of:
    applying a spatial filter to the target fluid map arranged in step (d) to attenuate noise artifacts.

4. The method according to claim 1, wherein step (c) includes estimating the spatial location using a geolocation estimator.

5. The method according to claim 1, further including, for each measurement point, the steps of:
    e) comparing the error associated with the CPL determined in step (iii) with a predetermined threshold; and
    f) discarding the CPL from the target fluid map, when the error is greater than a predetermined threshold.

6. The method according to claim 1, wherein step (c) includes determining, for each measurement point, a standard deviation of the CPL based on a first-order error propagation, the standard deviation of the CPL corresponding to the error associated with the CPL.

7. The method according to claim 1, further including, for each measurement point, the steps of:

e) detecting a received off-line pulse and at least one received on-line pulse in a received pulse burst;

f) integrating each received off-line pulse and the at least one received on-line pulse to determine, respectively, an off-line pulse energy and at least one on-line pulse energy;

g) normalizing the off-line pulse energy and the at least one on-line pulse energy by a corresponding transmitted off-line pulse energy and at least one transmitted on-line pulse energy, respectively; and h) determining the CPL using a ratio of the at least one normalized on-line pulse energy and the normalized off-line pulse energy.

8. The method according to claim 7, further including the step of:

adjusting the CPL by one or more predetermined factors, wherein the one or more predetermined factors include an atmospheric concentration length difference parameter, a fluid absorption cross-section parameter, a reflectivity ratio parameter and a system calibration parameter.

9. The method according to claim 8, wherein the reflectivity ratio parameter includes a reflectivity variability over the survey area, and step h) further includes correcting the reflectivity ratio parameter for the reflectivity variability.

10. The method according to claim 9, further including the steps of:

estimating a received energy for each of a predetermined number of measurement points of the survey area and a wavelength corresponding to each transmitted off-line pulse and the at least one transmitted on-line pulse;

determining return energy statistics based on the estimated received energy for each of the predetermined number of measurement points;

estimating regions of like reflectivity (ROLR) for the survey area using the determined return energy statistics of each of the predetermined number of measurement points; and approximating a reflectivity ratio parameter for each of the estimated ROLR using the corresponding determined return energy statistics of the ROLR.

11. A system for obtaining a target fluid map of a survey area using a differential absorption LIDAR (DIAL) system that transmits a plurality of pulse bursts toward the survey area, each transmitted pulse burst including an off-line pulse and at least one on-line pulse, the system comprising:

an input terminal for receiving a plurality of pulse bursts from the survey area, each pulse burst associated with a measurement point;

a concentration path length (CPL) estimator configured to determine, for each measurement point, a CPL corresponding to a respective on-line pulse and determine a spatial location associated with the respective CPL;

a quality factor error estimator configured to determine an error associated with the CPL for each of the measurement points; and a CPL map generator configured to arrange the CPL, for each measurement point, within the survey area to form the target fluid map.

12. The system according to claim 11, wherein the CPL estimator includes a reflectivity ratio corrector for correcting a reflectivity variability over the survey area based on return energy statistics for a predetermined number of measurement points.

13. The system according to claim 11, wherein the CPL estimator includes a geolocation estimator for estimating the spatial location from at least one spatial location measurement.

14. The system according to claim 11, wherein the quality factor error estimator determines, for each measurement point, a standard deviation of the CPL based on a first-order error propagation, the standard deviation corresponding to the associated error.

15. The system according to claim 11, wherein the CPL map generator compares the error determined by the quality factor error estimator, for each measurement point, with a predetermined threshold and discards the CPL from the target fluid map when the error is greater than a predetermined threshold.

16. The system according to claim 11, further comprising a spatial filter subsystem for attenuating noise artifacts in the target fluid map.

17. The system according to claim 11, further comprising a layer data applicator for applying spatial data to the target fluid map.

18. The system according to claim 11, further comprising a database configured to receive and store the plurality of pulse bursts from the survey area, the database providing the plurality of pulse bursts to the input terminal.

19. The system according to claim 11, further comprising a database configured to receive and store, for each measurement point, the CPL, the error and the spatial location, the database providing the CPL, the error and the spatial location for each measurement point to the CPL map generator.

20. The system according to claim 11, further comprising a database configured to receive and store the target fluid map arranged by the CPL map generator.

21. A concentration path length (CPL) estimator for estimating at least one CPL from a pulse burst received from a differential absorption LIDAR (DIAL) system, the pulse burst including an off-line pulse and at least one on-line pulse corresponding to a measurement point of a survey area, the CPL estimator comprising:

a pulse finder configured to detect the off-line pulse and the at least one on-line pulse of the pulse burst;

a pulse energy system configured to determine an off-line pulse energy and at least one on-line pulse energy associated with the detected off-line pulse and the detected at least one on-line pulse;

a reflectivity ratio corrector configured to correct a reflectivity ratio parameter for the received pulse burst; and a CPL processor configured to determine the at least one CPL using a ratio of the at least one on-line energy to the off-line energy, and the corrected reflectivity ratio parameter.

22. The CPL estimator according to claim 21, wherein the pulse energy system comprises:

a pulse energy integrator for integrating each received off-line pulse and each received on-line pulse to determine the off-line pulse energy and the at least one on-line pulse energy; and a pulse energy normalizer for normalizing the off-line pulse energy and the at least one on-line pulse energy by a corresponding transmitted pulse, wherein the CPL processor uses the at least one normalized on-line pulse energy and the normalized off-line pulse energy to compute the ratio.

23. The CPL estimator according to claim 21, wherein one or more predetermined parameters are used to determine the CPL and include an atmospheric concentration length difference parameter, a fluid absorption cross-section parameter and a system calibration parameter.

24. The CPL estimator according to claim 21, wherein the reflectivity ratio corrector (i) estimates regions of like reflectivity (ROLR) for the survey area using return energy statistics for a predetermined number of measurement points of the survey area and (ii) approximates a reflectivity ratio parameter for each of the estimated ROLR using the corresponding return energy statistics for the ROLR.

25. The CPL estimator according to claim 21, further comprising a geolocation estimator to estimate a spatial location of the CPL using at least one spatial location measurement from a global positioning system.

* * * * *